US010821221B2

(12) United States Patent
Takahashi et al.

(10) Patent No.: US 10,821,221 B2
(45) Date of Patent: Nov. 3, 2020

(54) ENCASED SYRINGE

(71) Applicant: GC Corporation, Shizuoka (JP)

(72) Inventors: Makoto Takahashi, Tokyo (JP); Manami Kurakazu, Tokyo (JP); Yuji Fujimaki, Tokyo (JP); Kaori Watanabe, Tokyo (JP)

(73) Assignee: GC Corporation, Shizuoka (JP)

( * ) Notice: Subject to any disclaimer, the term of this patent is extended or adjusted under 35 U.S.C. 154(b) by 165 days.

(21) Appl. No.: 16/088,155

(22) PCT Filed: Jan. 25, 2017

(86) PCT No.: PCT/JP2017/002578
§ 371 (c)(1),
(2) Date: Sep. 25, 2018

(87) PCT Pub. No.: WO2017/169038
PCT Pub. Date: Oct. 5, 2017

(65) Prior Publication Data
US 2020/0016322 A1    Jan. 16, 2020

(30) Foreign Application Priority Data
Mar. 31, 2016   (JP) ................................. 2016-071321

(51) Int. Cl.
*A61M 5/00*      (2006.01)
*A61M 5/31*      (2006.01)

(52) U.S. Cl.
CPC .......... *A61M 5/002* (2013.01); *A61M 5/3148* (2013.01); *A61M 5/008* (2013.01)

(58) Field of Classification Search
USPC ......................................................... 206/364
See application file for complete search history.

(56) References Cited

U.S. PATENT DOCUMENTS 8,925,723 B2 *   1/2015   Folchini ................ A61M 5/002
                                                                                    206/364
2002/0141950 A1  10/2002  Chen
(Continued)

FOREIGN PATENT DOCUMENTS

CN        1134117     10/1996
EP        0739638     10/1996
(Continued)

OTHER PUBLICATIONS

International Search Report for PCT/JP2017/002578 dated Apr. 11, 2017.
(Continued)

*Primary Examiner* — Jacob K Ackun
(74) *Attorney, Agent, or Firm* — IPUSA, PLLC

(57) ABSTRACT

An embodiment of the present invention is an encased syringe in which a prefilled syringe is accommodated in a case. The prefilled syringe includes a cylindrical syringe body filled with a foamable material and a plunger pressed into the syringe body on one end side. The case includes a body accommodating part faulted to be depressed along the shape of the syringe body to accommodate the syringe body and a plunger accommodating part formed to be depressed along the shape of the plunger to accommodate the plunger. The length of the plunger accommodating part is smaller than the length of the plunger in an axial direction of the prefilled syringe.

6 Claims, 2 Drawing Sheets

(56) References Cited

U.S. PATENT DOCUMENTS

| | | | |
|---|---|---|---|
| 2007/0003494 A1 | 1/2007 | Mori et al. | |
| 2014/0078854 A1* | 3/2014 | Head | B01F 11/0005 366/111 |
| 2015/0129442 A1 | 5/2015 | Head et al. | |
| 2016/0279039 A1* | 9/2016 | Giniger | A61K 8/19 |
| 2018/0110805 A9* | 4/2018 | Shanler | A61P 17/00 |
| 2018/0344582 A1* | 12/2018 | Kim | A61K 8/25 |

FOREIGN PATENT DOCUMENTS

| | | |
|---|---|---|
| JP | H08-057050 | 3/1996 |
| JP | 2004-035024 | 2/2004 |
| JP | U3112395 | 8/2005 |
| JP | 2006-168768 | 6/2006 |
| JP | 2007-008874 | 1/2007 |
| JP | 2009-242290 | 10/2009 |
| JP | 2011-005182 | 1/2011 |
| JP | 2014-162532 | 9/2014 |

OTHER PUBLICATIONS

Chinese Office Action dated Jun. 1, 2020 (CN Patent Application No. 201780020459.X).

* cited by examiner

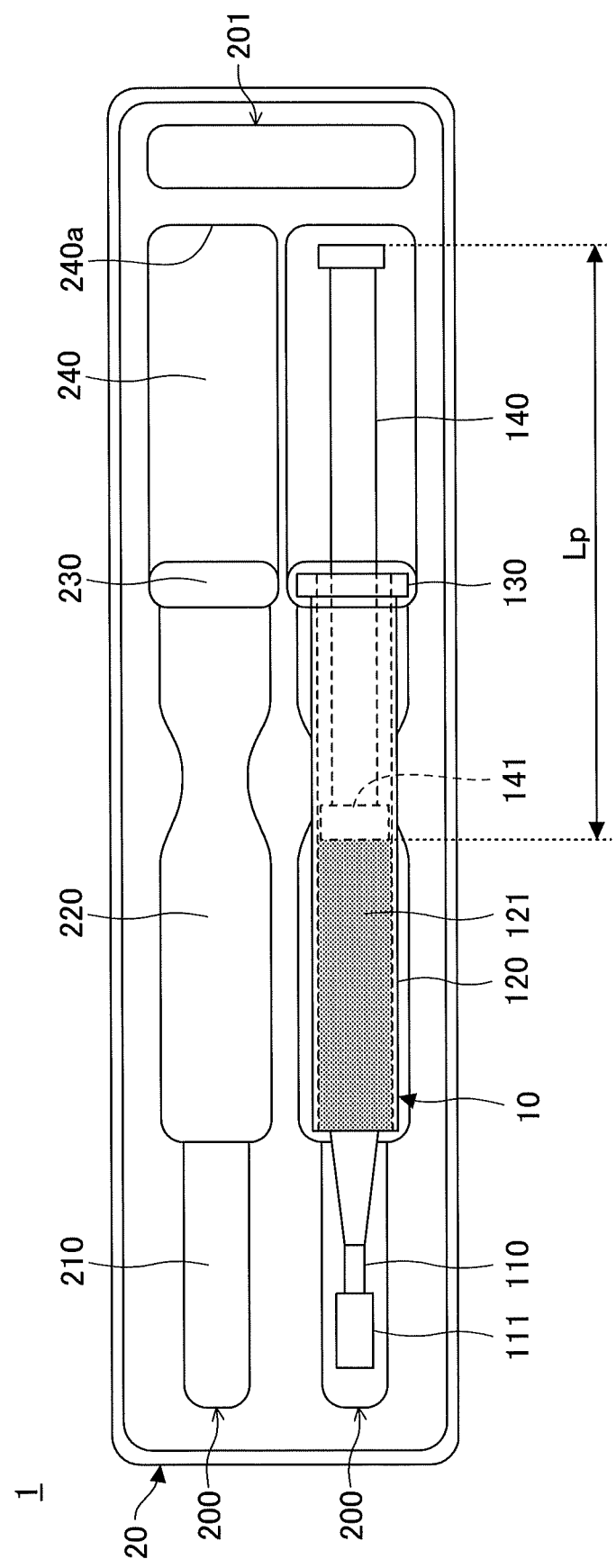

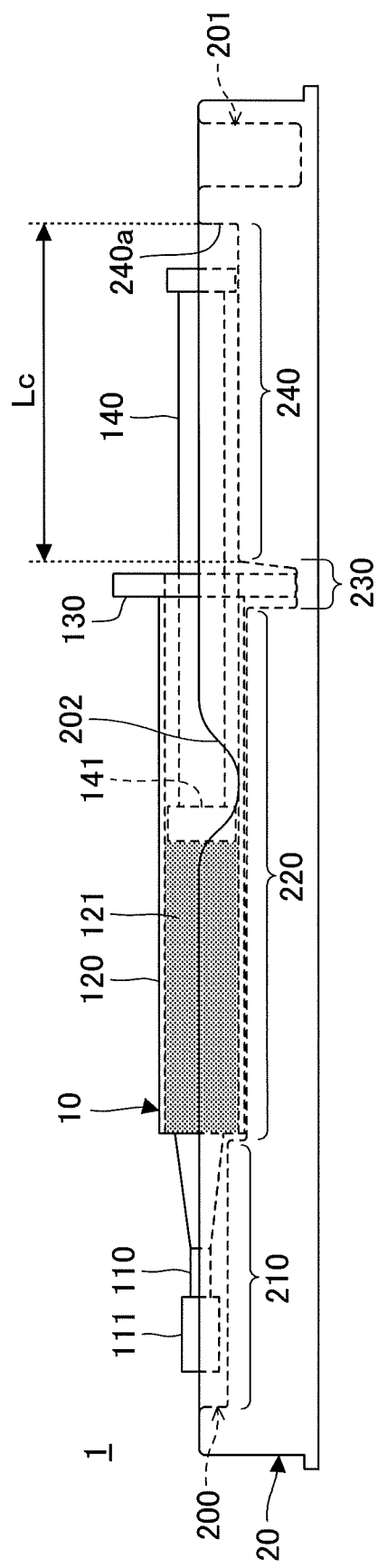

ENCASED SYRINGE

TECHNICAL FIELD

The present invention relates to encased syringes.

BACKGROUND ART

A tooth bleaching composition that contains hydrogen peroxide or a hydrogen peroxide derivative to have an improved tooth bleaching effect is known (see, for example, Patent Document 1). In terms of convenience at the time of use and prevention of contamination, such a tooth bleaching composition is provided, being preloaded in a syringe that includes a syringe body and a plunger, for example.

A syringe preloaded with a medicine such as a tooth bleaching composition is referred to as a prefilled syringe, and is distributed, being accommodated in a case.

PRIOR ART DOCUMENT

Patent Document

Patent Document 1: Japanese Laid-Open Patent Publication No. 2009-242290

SUMMARY OF THE INVENTION

Problems to be Solved by the Invention

Here, for example, when the above-described hydrogen peroxide or hydrogen peroxide derivative decomposes to generate air bubbles of a decomposition product of hydrogen peroxide, the internal pressure of the syringe body increases, so that the plunger may be displaced in a direction to be removed from the syringe body. When the plunger is thus displaced, the plunger may be removed from the syringe body to cause the leakage of the medicine, or the syringe may be displaced from the case to be broken, making it impossible to be used as a prefilled syringe.

An embodiment of the present invention has been made in view of the above, and has an object of providing an encased syringe that can prevent the displacement of a plunger.

Means for Solving the Problems

An embodiment of the present invention is an encased syringe in which a prefilled syringe is accommodated in a case. The prefilled syringe includes a cylindrical syringe body filled with a foamable material and a plunger pressed into the syringe body on one end side. The case includes a body accommodating part formed to be depressed along the shape of the syringe body to accommodate the syringe body and a plunger accommodating part formed to be depressed along the shape of the plunger to accommodate the plunger. The length of the plunger accommodating part is smaller than the length of the plunger in an axial direction of the prefilled syringe.

Effects of the Invention

According to an embodiment of the present invention, an encased syringe that can prevent the displacement of a plunger is provided.

BRIEF DESCRIPTION OF THE DRAWINGS

FIG. 1 is a plan view illustrating an encased syringe according to this embodiment.

FIG. 2 is a front view illustrating the encased syringe according to this embodiment.

EMBODIMENT OF THE INVENTION

An embodiment of the present invention is described below based on the drawings. In each drawing, the same components are given the same reference numeral, and a repetitive description may be omitted.

FIGS. 1 and 2 illustrate an encased syringe according to this embodiment.

According to an encased syringe 1, a prefilled syringe 10 is accommodated in a case 20 as illustrated in FIGS. 1 and 2.

The prefilled syringe 10 includes a nozzle 110, a syringe body 120, and a plunger 140. The nozzle 110, the syringe body 120, and the plunger 140 are famed of, for example, plastic. The syringe body 120 is filled with a tooth bleaching composition 121. By pushing the plunger 140 into the syringe body 120, a user of the prefilled syringe 10 can extrude the tooth bleaching composition 121 from the syringe body 120 to discharge the tooth bleaching composition 121 from the discharge orifice of the nozzle 110.

The nozzle 110 is provided at an end of the syringe body 120. The nozzle 110 has a discharge orifice at an end opposite to the syringe body 120, and discharges the tooth bleaching composition 121 extruded from the syringe body 120. When the prefilled syringe 10 is accommodated in the case 20 or the prefilled syringe 10 is not in use, a cap 111 is attached to the nozzle 110 to close its discharge orifice as illustrated in FIGS. 1 and 2.

The syringe body 120 is shaped into a cylinder, and is filled with the tooth bleaching composition 121. The nozzle 110 is provided at one end of the syringe body 120, and the plunger 140 is inserted in the syringe body 120 through an opening at the other end of the syringe body 120. An outward projecting flange 130 is formed at the end of the syringe body 120 opposite to the nozzle 110.

The plunger 140 is shaped into a pillar, and is inserted in the syringe body 120 on one end side. A gasket 141 is attached to the end of the plunger 140 inserted in the syringe body 120. The gasket 141 is formed of, for example, a resin material such as rubber, and hermetically seals the internal space of the syringe body 120. When the plunger 140 is pushed into the syringe body 120, the tooth bleaching composition 121 extruded by the gasket 141 is discharged from the nozzle 110.

Here, the tooth bleaching composition 121 is an example of the material loaded into the syringe body 120 of the prefilled syringe 10. The tooth bleaching composition 121 is applied and adheres to a tooth to bleach the tooth in which a pigment has deposited, for example.

The material loaded into the prefilled syringe 10 is not limited to the tooth bleaching composition 121 as long as the material is a foamable material.

The tooth bleaching composition 121 contains hydrogen peroxide or a hydrogen peroxide derivative, and preferably, further contains a thickener and a solvent.

Hydrogen peroxide or hydrogen peroxide derivatives possess bleaching properties.

Examples of hydrogen peroxide derivatives include urea peroxide, perborate, percarbonate, superphosphate, persulfates, calcium peroxide, magnesium peroxide, and hydrogen peroxide polyvinylpyrrolidone. Urea peroxide is preferably used as a hydrogen peroxide derivative.

The tooth bleaching composition 121 contains hydrogen peroxide or a hydrogen peroxide derivative to be a foamable material that generates air bubbles of a decomposition product of hydrogen peroxide.

The content of hydrogen peroxide or a hydrogen peroxide derivative in the tooth bleaching composition 121 is preferably 1% by mass to 30% by mass in amount in terms of peroxide derivative. When the content of hydrogen peroxide or a hydrogen peroxide derivative in the tooth bleaching composition 121 is 1% by mass or more, the bleaching effect of the tooth bleaching composition 121 is easy to obtain. When the content of hydrogen peroxide or a hydrogen peroxide derivative in the tooth bleaching composition 121 is 30% by mass or less, the storage stability of the tooth bleaching composition 121 is improved.

Examples of thickeners include organic thickeners such as sodium carboxymethyl cellulose, sodium alginate, propylene glycol alginate, carboxypolymethylene, carboxymethyl cellulose, sodium carboxymethyl cellulose, calcium carboxymethyl cellulose, a methyl vinyl ether-maleic anhydride copolymer, dimethyl polysiloxane, sodium starch glycolate, sodium starch phosphate ester, sodium polyacrylate, methyl cellulose, hydroxymethyl cellulose, hydroxyethyl cellulose, hydroxypropyl cellulose, polyvinylpyrrolidone, an acrylic acid-behenic acid copolymer, and crystalline cellulose; natural thickeners such as guar gum, carob bean gum, tara gum, tamarind seed gum, gum arabic, tragacanth gum, karaya gum, alginic acid, carrageenan, xanthan gum, gellan gum, curdlan, chitin, chitosan, and chitosamine; and inorganic thickeners such as calcium carbonate, calcium silicate, magnesium silicate, sodium magnesium silicate, lithium magnesium sodium silicate, silica powders, various glasses, amorphous hydrated silicic acid, and fumed silica. Polyvinylpyrrolidone, carboxypolymethylene, or a methyl vinyl ether-maleic anhydride copolymer is preferably used as a thickener.

The thickener content in the tooth bleaching composition 121 is preferably 0.5% by mass to 30% by mass. When the thickener content in the tooth bleaching composition 121 is 0.5% by mass or more, the tooth bleaching composition 121 easily adheres to teeth because of high viscosity. When the thickener content in the tooth bleaching composition 121 is 30% by mass or less, the tooth bleaching composition 121 is soft and easy to extrude from the syringe body 120.

Water and/or alcohol may be used as a solvent.

As alcohol, it is preferable to use ethanol, stearyl alcohol, 1-propanol, 2-propanol or 2-methyl-2-propanol, polyethylene glycol monomethyl ether, polyhydric alcohol in terms of teeth adhesion operability.

As polyhydric alcohol, it is preferable to use polyglycerol such as glycerin or diglycerin, ethylene glycol, diethylene glycol, polyethylene glycol, propylene glycol, dipropylene glycol, polypropylene glycol, 1,2-pentanediol, 1,2-hexanediol, 1,2-octanediol, sorbitol, mannitol, or any mixture thereof because of excellent safety and good affinity with teeth.

As a solvent, it is preferable to use water and/or polyhydric alcohol, and as polyhydric alcohol, it is preferable to use glycerin, polyethylene glycol, or propylene glycol.

The solvent content in the tooth bleaching composition 121 is preferably 50% by mass to 85% by mass. When the solvent content in the tooth bleaching composition 121 is 50% by mass or more, the tooth bleaching composition 121 is soft and easy to extrude from the syringe body 120. When the solvent content in the tooth bleaching composition 121 is 85% by mass or less, the storage stability of the tooth bleaching composition 121 is improved.

In addition to hydrogen peroxide or a hydrogen peroxide derivative, a thickener, and a solvent, the tooth bleaching composition 121 may further contain, for example, a metal oxide such as titanium oxide, zinc oxide, or titanium oxynitride, titanium oxide doped with nitrogen, a metal salt, metal powder, a catalyst for activating hydrogen peroxide, a calcium chelating agent, a pH adjusting agent, etc.

The case 20 is, for example, formed into a box shape with an open bottom, using a plastic sheet, and an upper surface of the case 20 is depressed to form a syringe accommodating part 200, a shock absorbing part 201, and a recess 202. Furthermore, the case 20 may include a covering that covers the prefilled syringe 10 placed in the syringe accommodating part 200.

The syringe accommodating part 200 is famed in the upper surface of the case 20 to be depressed along the shape of the prefilled syringe 10. The prefilled syringe 10 is placed in the syringe accommodating part 200.

The shock absorbing part 201 is formed in the upper surface of the case 20 to be depressed at a position different than the syringe accommodating part 200, and for example, absorbs impact at the time of the falling of the encased syringe 1 or vibrations at the time of transportation of the encased syringe 1 to prevent the breakage of the encased syringe 1.

The recess 202 is formed in the upper surface of the case 20 to be depressed near the center of the syringe body 120 of the prefilled syringe 10 in its axial direction as illustrated in FIG. 2. This makes it easy for a user of the prefilled syringe 10 to take the prefilled syringe 10 out of the case 20 by holding the syringe body 120.

According to the encased syringe 1, while two syringe accommodating parts 200 are formed in the case 20, the number of syringe accommodating parts 200 formed in the case 20 is not limited to two.

Here, FIG. 1 illustrates that the prefilled syringe 10 is taken out of one of the syringe accommodating parts 200 in order to show the shape of the syringe accommodating parts 200.

Furthermore, the configurations of the shock absorbing part 201 and the recess 202, such as a shape, a position, and a number, are not limited to the configurations illustrated in FIGS. 1 and 2.

The syringe accommodating part 200 includes a nozzle accommodating part 210, a body accommodating part 220, a flange accommodating part 230, and a plunger accommodating part 240.

The nozzle accommodating part 210 is formed in the upper surface of the case 20 to be depressed into a semicylindrical shape along the shape of the nozzle 110 and the cap 111 of the prefilled syringe 10. The nozzle accommodating part 210 accommodates the nozzle 110 to which the cap 111 is attached.

The body accommodating part 220 is formed in the upper surface of the case 20 to be depressed into a semicylindrical shape along the shape of the syringe body 120 of the prefilled syringe 10. The body accommodating part 220 accommodates the syringe body 120 of the prefilled syringe 10.

The flange accommodating part 230 is formed in the upper surface of the case 20 to be depressed into a semicylindrical shape along the shape of the flange 130 provided on the syringe body 120 of the prefilled syringe 10. The flange accommodating part 230 accommodates the flange 130 of the prefilled syringe 10.

The plunger accommodating part 240 is formed in the upper surface of the case 20 to be depressed into a semicylindrical shape along the shape of the plunger 140 of the prefilled syringe 10. The plunger accommodating part 240 accommodates the plunger 140 of the prefilled syringe 10.

The nozzle accommodating part 210, the body accommodating part 220, the flange accommodating part 230, and the plunger accommodating part 240 differ in length (width in a left-right direction in FIG. 1) and depth from the top in accordance with the shape of each part of the prefilled syringe 10.

The syringe body 120 is locked by the step between the nozzle accommodating part 210 and the body accommodating part 220 that are different in depth, so that the displacement of the prefilled syringe 10 accommodated in the syringe accommodating part 200 toward the nozzle 110 side in an axial direction (a top-bottom direction of FIGS. 1 and 2) of the prefilled syringe 10 accommodated in the syringe accommodating part 200 is restricted. Furthermore, the flange 130 of the prefilled syringe 10 is locked by the flange accommodating part 230, so that the displacement of the prefilled syringe 10 accommodated in the syringe accommodating part 200 in the axial direction is restricted.

Furthermore, a length Lc of the plunger accommodating part 240 is smaller than a length Lp of the plunger 140 (including the gasket 141) in the axial direction of the prefilled syringe 10 accommodated in the syringe accommodating part 200.

Here, in the tooth bleaching composition 121 loaded in the syringe body 120, for example, air bubbles may be generated because of a decomposition product generated by decomposition of a hydrogen peroxide derivative over time or decomposition of a hydrogen peroxide derivative due to applied heat to increase the internal pressure of the syringe body 120, thereby pushing back the plunger 140 to the opposite side from the nozzle 110.

In such a case, because the length Lc of the plunger accommodating part 240 is smaller than the length Lp of the plunger 140, the end of the plunger 140 opposite to the gasket 141 contacts a wall face 240a of the plunger accommodating part 240 before removal of the plunger 140 from the syringe body 120. Furthermore, according to the prefilled syringe 10, the syringe body 120 and the flange 130 are locked by the syringe accommodating part 200, so that the plunger 140 is restricted from being displaced in the axial direction and is almost fixed.

By the above-described configuration, for example, even when the tooth bleaching composition 121 foams to push back the plunger 140, the end of the plunger 140 contacts the wall face 240a of the plunger accommodating part 240 to prevent a further displacement of the plunger 140 before the plunger 140 is removed from the syringe body 120. By thus restricting a displacement of the plunger 140 in the axial direction, the occurrence of troubles such as removal of the plunger 140 from the syringe body 120 and removal of the prefilled syringe 10 from the case 20 is reduced.

As described above, according to the encased syringe 1, even when the tooth bleaching composition 121 loaded in the syringe body 120 foams, the displacement of the plunger 140 in the axial direction is controlled. Accordingly, the occurrence of troubles due to the displacement of the plunger 140 in the axial direction is reduced.

An encased syringe according to this embodiment is described above. The present invention, however, is not limited to the above-described embodiment, and variations and modifications may be made without departing from the scope of the present invention.

The present international application is based on and claims priority to Japanese patent application No. 2016-071321, filed on Mar. 31, 2016, the entire contents of which are hereby incorporated herein by reference.

DESCRIPTION OF THE REFERENCE NUMERALS 1 encased syringe
10 prefilled syringe
20 case
110 nozzle
120 syringe body
121 tooth bleaching composition
130 flange
140 plunger
200 syringe accommodating part
210 nozzle accommodating part
220 body accommodating part
230 flange accommodating part
240 plunger accommodating part

The invention claimed is:

1. An encased syringe in which a prefilled syringe is accommodated in a case, wherein
the prefilled syringe includes
a cylindrical syringe body filled with a foamable material;
a nozzle provided at an end of the syringe body; and
a plunger pressed into the syringe body on one end side,
the case includes
a body accommodating part formed to be depressed along a shape of the syringe body to accommodate the syringe body;
a nozzle accommodating part formed to be depressed along a shape of the nozzle to accommodate the nozzle, the nozzle accommodating part being different in depth from the body accommodating part; and
a plunger accommodating part formed to be depressed along a shape of the plunger to accommodate the plunger,
a length of the plunger accommodating part is smaller than a length of the plunger in an axial direction of the prefilled syringe, and
the syringe body is locked by a step between the nozzle accommodating part and the body accommodating part that are different in depth, so that a displacement of the prefilled syringe accommodated in the case toward a side of the nozzle in an axial direction of the prefilled syringe accommodated in the case is restricted.

2. The encased syringe as claimed in claim 1, wherein
a flange is formed on the syringe body, and
the case includes a flange accommodating part formed to be depressed along a shape of the flange to accommodate the flange.

3. The encased syringe as claimed in claim 1, wherein the foamable material contains hydrogen peroxide or a hydrogen peroxide derivative.

4. The encased syringe as claimed in claim 3, wherein the foamable material further contains a thickener and a solvent.

5. The encased syringe as claimed in claim 4, wherein, in the foamable material,
a content of the hydrogen peroxide or the hydrogen peroxide derivative is 1% by mass to 30% by mass in amount in terms of hydrogen peroxide, and
a content of the thickener is 0.5% by mass to 30% by mass, and
a content of the solvent is 50% by mass to 85% by mass.

6. The encased syringe as claimed in claim 1, wherein the body accommodating part is deeper than the nozzle accommodating part.

\* \* \* \* \*